US011173031B2

(12) United States Patent
Naor et al.

(10) Patent No.: US 11,173,031 B2
(45) Date of Patent: Nov. 16, 2021

(54) ASSISTIVE DEVICE FOR A CARDIAC VALVE

(71) Applicant: Mitrassist Medical Ltd., Caesarea (IL)

(72) Inventors: Gil Naor, Hofit (IL); Yiftah Neta, Gilon (IL); Avner Geva, Tel-Aviv (IL)

(73) Assignee: Mitrassist Medical Ltd., Caesarea (IL)

( * ) Notice: Subject to any disclaimer, the term of this patent is extended or adjusted under 35 U.S.C. 154(b) by 0 days.

(21) Appl. No.: 15/527,330

(22) PCT Filed: Nov. 17, 2015

(86) PCT No.: PCT/IL2015/051105
§ 371 (c)(1),
(2) Date: May 17, 2017

(87) PCT Pub. No.: WO2016/079734
PCT Pub. Date: May 26, 2016

(65) Prior Publication Data
US 2018/0078361 A1 Mar. 22, 2018

Related U.S. Application Data

(60) Provisional application No. 62/080,631, filed on Nov. 17, 2014.

(51) Int. Cl.
*A61F 2/06* (2013.01)
*A61F 2/24* (2006.01)

(52) U.S. Cl.
CPC .......... *A61F 2/246* (2013.01); *A61F 2/2412* (2013.01); *A61F 2/2448* (2013.01); *A61F 2230/0015* (2013.01)

(58) Field of Classification Search
CPC .......... A61B 17/12122; A61B 10/0045; A61B 17/0487; A61B 1/00009;
(Continued)

(56) References Cited

U.S. PATENT DOCUMENTS 4,373,216 A * 2/1983 Klawitter .............. A61F 2/2403
623/2.22
2005/0070999 A1 3/2005 Spence
(Continued)

FOREIGN PATENT DOCUMENTS

| CN | 101056596 | 10/2007 |
| CN | 104042359 | 9/2014 |

(Continued)

OTHER PUBLICATIONS

International Preliminary Report on Patentability dated Jun. 1, 2017 From the International Bureau of WIPO Re. Application No. PCT/IL2015/0511109. (12 Pages).
(Continued)

*Primary Examiner* — Ann Schillinger

(57) ABSTRACT

A device for reducing heart valve regurgitation including a plug for placing between natural heart valve leaflets, the plug shaped so that, upon systole, the natural heart leaflets coapt upon the plug, a frame attached to the plug by a bridging element, for supporting the plug between the natural heart valve leaflets, the frame having at least one dimension in a plane of the heart valve annulus which is wider than the diameter of the heart valve annulus, and a plurality of anchors attached to the device, for preventing the device from being swept upstream of the heart valve annulus upon systole. Related apparatus and methods are also described.

19 Claims, 9 Drawing Sheets

(58) Field of Classification Search
CPC ......... A61B 2018/00351; A61F 2/2427; A61F 2220/0016; A61F 2/2418; A61F 2250/006; A61F 2/246; A61F 2/01; A61F 2/2412; A61F 2/2487; A61F 2/24; A61F 2/2451; A61F 2/2457; A61F 2/2463
See application file for complete search history.

(56) References Cited

U.S. PATENT DOCUMENTS

| | | | |
|---|---|---|---|
| 2010/0298929 A1* | 11/2010 | Thornton | A61B 17/00234 623/2.1 |
| 2011/0137397 A1* | 6/2011 | Chau | A61F 2/246 623/1.11 |
| 2017/0367822 A1 | 12/2017 | Naor et al. | |

FOREIGN PATENT DOCUMENTS

| | | | |
|---|---|---|---|
| EP | 2478868 | 7/2012 | |
| EP | 2478868 A1 * | 7/2012 | ......... A61B 17/0057 |
| WO | WO 2009/053952 | 4/2009 | |
| WO | WO 2016/079734 | 5/2016 | |

OTHER PUBLICATIONS

International Search Report and the Written Opinion dated May 17, 2016 From the International Searching Authority Re. Application No. PCT/IL2015/051109.

Notification of Office Action and Search Report dated Jul. 3, 2018 From the State Intellectual Property Office of the People's Republic of China Re. Application No. 201580073643.1 and Its Translation Into English. (23 Pages).

Official Action dated Jan. 17, 2019 From US Patent and Trademark Office Re. U.S. Appl. No. 15/527,332. (9 pages).

Notification of Office Action dated Dec. 9, 2019 From the National Intellectual Property Administration of the People's Republic of China Re. Application No. 201580073643.1 and Its Translation Into English. (23 Pages).

* cited by examiner

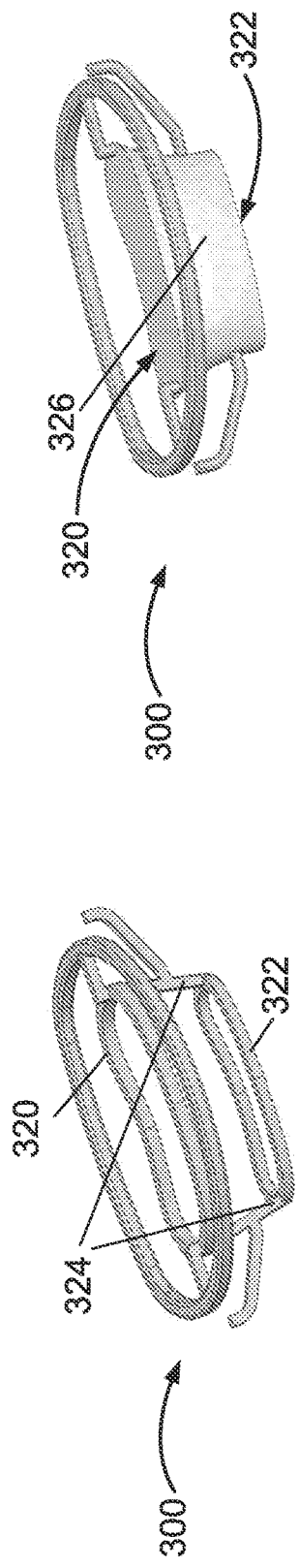
FIGURE 4B
FIGURE 4A
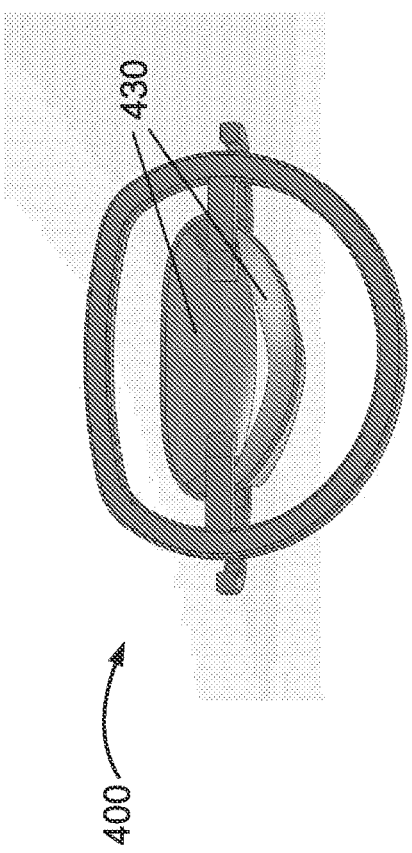
FIGURE 5
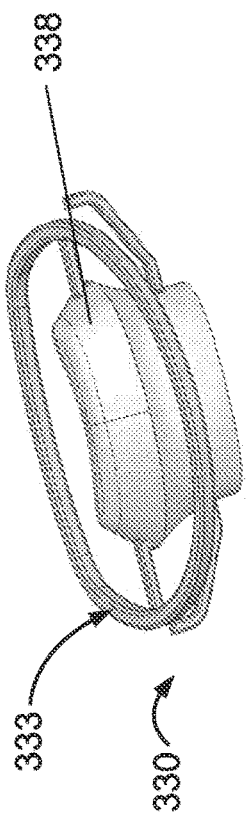
FIGURE 4C

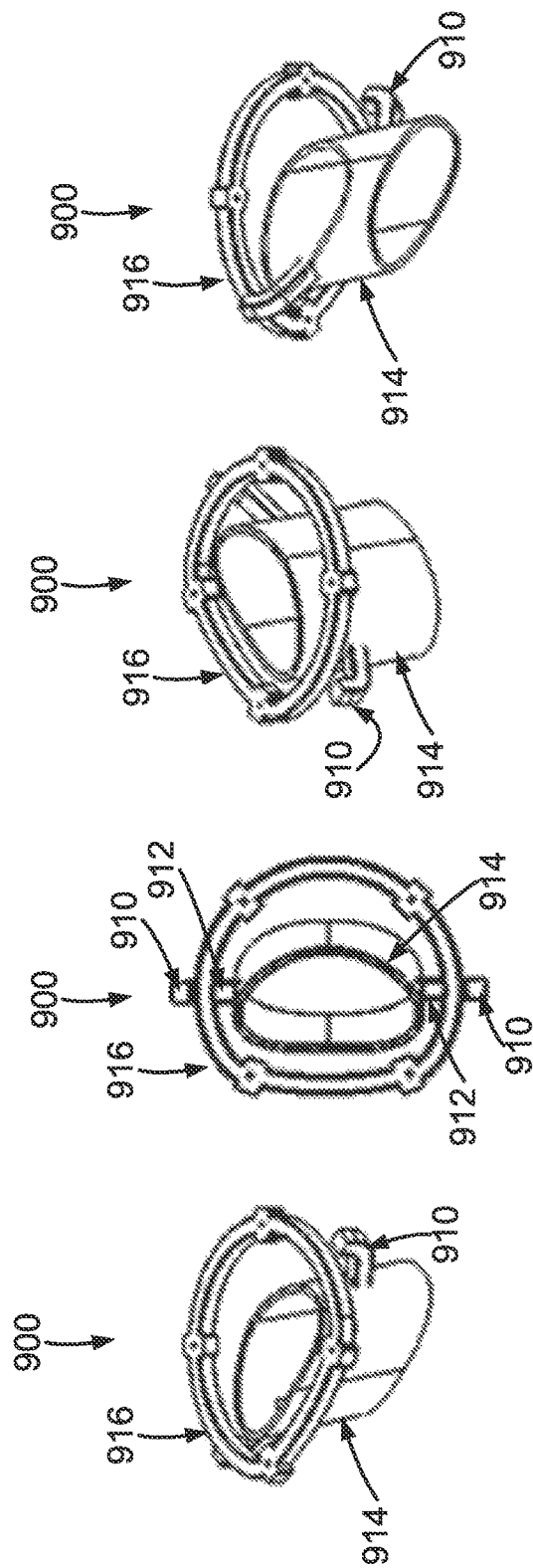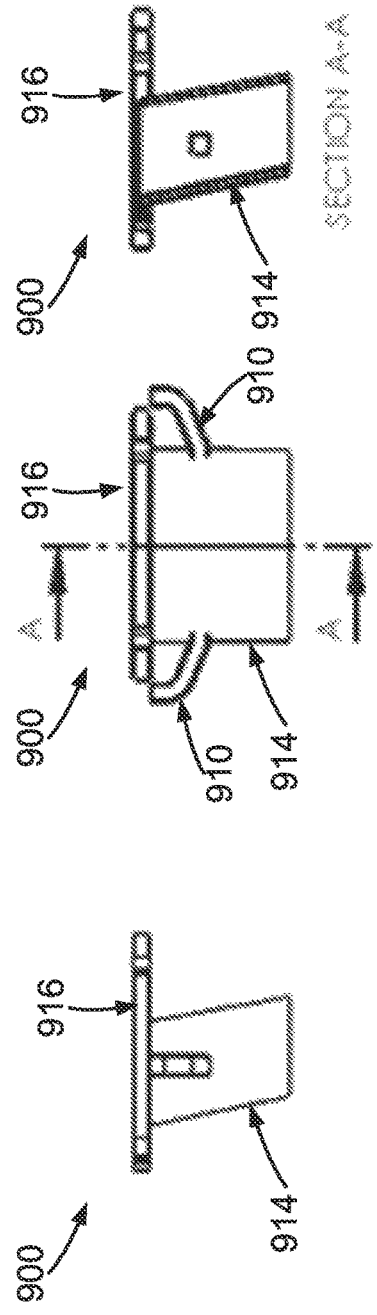

ASSISTIVE DEVICE FOR A CARDIAC VALVE

RELATED APPLICATIONS

This application is a National Phase of PCT Patent Application No. PCT/IL2015/051105 having International filing date of Nov. 17, 2015, which claims the benefit of priority under 35 USC § 119(e) of U.S. Provisional Patent Application No. 62/080,631 filed on Nov. 17, 2014. The contents of the above applications are all incorporated by reference as if fully set forth herein in their entirety.

FIELD AND BACKGROUND OF THE INVENTION

The present invention, in some embodiments thereof, relates to methods and devices for reducing heart valve regurgitation, and more particularly, but not exclusively, to reducing mitral valve regurgitation.

The mitral valve and the tricuspid valve are unidirectional heart valves which separate the left and right atria respectively, from corresponding heart ventricles. These valves have a distinct anatomical and physiological structure, having two (mitral) or three (tricuspid) sail-like leaflets connected to a sub-valvular mechanism of strings (chordae tendinae) and papillary muscles forming a part of the heart's ventricular shape, function and size.

The heart has four chambers: the right and left atria, and the right and left ventricles. The atria receive blood and then pump it into the ventricles, which then pump it out into the body.

Synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves which are supposed to ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, intra-ventricular pressure rises above the pressure in the atrium and pushes the mitral valve shut.

As noted above, these valves feature a plurality of leaflets connected to chordae tendinae and papillary muscles, which allow the leaflets to resist the high pressure developed during contractions (pumping) of the left and right ventricles. In a healthy heart, the chordae become taut, preventing the leaflets from being forced into the left or right atria and inverted. Prolapse is a term used to describe a condition wherein coaptation edges of each leaflet initially may coapt and close, but then the leaflets rise higher, the edges separate, and the valve leaks. This is normally prevented by a contraction of the papillary muscles and by the normal length of the chordae. Contraction of the papillary muscles is usually simultaneous with the contraction of the ventricle and serves to keep healthy valve leaflets tightly shut at peak contraction pressures exerted by the ventricle.

Valve malfunction can result from the chordae becoming stretched, and in some cases tearing. When a chord tears, the result is a flailed leaflet. Also, a normally structured valve may not function properly because of an enlargement of the valve annulus pulling the leaflets apart. This condition is referred to as a dilation of the annulus and generally results from heart muscle failure. In addition, the valve may be defective at birth or because of an acquired disease, usually infectious or inflammatory.

Diseases of the valves can cause either narrowing (stenosis) or dilatation (regurgitation, insufficiency) of the valve, or a combination of those. Surgical treatment for repair or replacement of the valves typically includes an open-heart procedure, extracorporeal circulation and, if replaced, a complete or partial resection of the diseased valve.

Additional background art includes:
PCT patent application number IL2014/050414 of Naor;
PCT Published Patent Application WO2010/106438 of Naor et al;
PCT published patent application number WO2004/030568 of Macoviak et al;
US published patent application number 2011/0208297 of Tuval et al;
US published patent application number 2010/0280606 of Naor;
US published patent application number 2007/0270943 of Solem et al;
US published patent application number 2007/0185571 of Kapadia et al;
US published patent application number 2006/0058871 of Zakay et al;
US published patent application number 2003/0199975 of Gabbay;

The disclosures of all references mentioned above and throughout the present specification, as well as the disclosures of all references mentioned in those references, are hereby incorporated herein by reference.

SUMMARY OF THE INVENTION

The present invention, in some embodiments thereof, relates to methods and devices for reducing heart valve regurgitation, and more particularly, but not exclusively, to reducing mitral valve regurgitation.

An aspect of some embodiments includes positioning a plug or a stopper-like element in a region of the mitral leakage. With the plug in place, the native leaflets close against the plug structure. During closure, the native anterior and posterior leaflets interface with the plug, effectively creating new non-leaking cooptation lines.

An aspect of some embodiments includes placing a structure between heart valve leaflets, which on the outer surface coapts with natural heart valve leaflets, and includes an inner surface defining a lumen containing a one-way valve. The one way valve is optionally open when blood flows in the downstream direction, and closes against blood regurgitating back upstream. The one way valve thus joins in the functioning of the natural heart valve.

According to an aspect of some embodiments of the present invention there is provided a device for reducing heart valve regurgitation including a plug for placing between natural heart valve leaflets, the plug shaped so that, upon systole, the natural heart leaflets coapt upon the plug, a frame attached to the plug by a bridging element, for supporting the plug between the natural heart valve leaflets, the frame having at least one dimension in a plane of the heart valve annulus which is wider than the diameter of the heart valve annulus, and a plurality of anchors attached to the device, for preventing the device from being swept upstream of the heart valve annulus upon systole.

According to some embodiments of the invention, the plug includes a one-directional flow valve.

According to some embodiments of the invention, a cross section of the plug parallel to the plane of the heart valve annulus is kidney-shaped.

According to some embodiments of the invention, a top of the plug presents a stream-lined shape to a direction of blood flow. According to some embodiments of the invention, a top of the plug is higher than the frame relative to a direction of blood flow. According to some embodiments of the invention, a top of the plug is lower than the frame relative to a direction of blood flow.

According to some embodiments of the invention, a center of the plug is shifted relative to a center of the frame, in a plane parallel to a plane of the frame.

According to some embodiments of the invention, the frame is an expandable metal shape.

According to some embodiments of the invention, a length of the plug along a direction of blood flow is at least 5 millimeters.

According to some embodiments of the invention, the anchors are located so as to be at heart valve commissures when the device is in place in the heart.

According to some embodiments of the invention, the anchors are located so as to allow the natural heart valve leaflets to move away from the plug.

According to some embodiments of the invention, the anchors are attached to the plug. According to some embodiments of the invention, the anchors are attached to the frame.

According to some embodiments of the invention, the anchors are attached to the bridging elements.

According to some embodiments of the invention, the bridging element includes two bridging elements.

According to an aspect of some embodiments of the present invention there is provided a method for reducing heart valve regurgitation including inserting a device into a heart valve, the device including a plug for placing between natural heart valve leaflets, the plug shaped so that, upon systole, the natural heart leaflets coapt upon the plug, a frame attached to the plug by a bridging element, for supporting the plug between the natural heart valve leaflets, the frame having at least one dimension in a plane of the heart valve annulus which is wider than the diameter of the heart valve annulus, and a plurality of anchors attached to the device, for preventing the device plug from being swept upstream of the heart valve annulus upon systole, placing the plug between natural heart valve leaflets, placing a portion of the frame upstream of the heart valve annulus, and placing the anchors downstream of the heart valve annulus.

According to some embodiments of the invention, the placing the anchors downstream of the heart valve annulus includes placing the anchors downstream of the heart valve annulus at locations of the heart valve commissure.

According to some embodiments of the invention, a surgeon uses imaging of the natural heart in order to determine a height, relative to a direction of blood flow, of a top of the plug relative to a height of the frame, and select a device with a plug having such a height for insertion into the heart valve.

According to some embodiments of the invention, a surgeon uses imaging of the natural heart in order to determine a height, relative to a direction of blood flow, of a top of the plug relative to a height of the frame, and set the height of the top of the plug relative to the height of the frame based, at least in part, on the imaging.

According to some embodiments of the invention, the heart valve is the mitral valve and the plug is kidney-shaped.

According to some embodiments of the invention, the heart valve is the mitral valve and the device includes two anchors. According to some embodiments of the invention, the two anchors are located so as to pass through the mitral valve at commissures of the mitral valve.

According to some embodiments of the invention, the heart valve is the mitral valve and the device includes two bridging elements.

According to some embodiments of the invention, further including suturing the device to the heart.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 4A is a simplified isometric line drawing of a wire frame construction which forms part of a device constructed according to an example embodiment of the invention;

FIG. 4B is a simplified isometric line drawing of the wire frame construction of FIG. 4A and an additional plug cover material;

FIG. 4C is an isometric view of a device constructed according to another example embodiment of the invention;

FIG. 5 is an isometric view of a device constructed according to yet another example embodiment of the invention;

FIGS. 9A-9G are simplified illustrations of a device 900 for reducing mitral valve regurgitation according to still another example embodiment of the invention.

DESCRIPTION OF SPECIFIC EMBODIMENTS OF THE INVENTION

The present invention, in some embodiments thereof, relates to methods and devices for reducing heart valve regurgitation, and more particularly, but not exclusively, to reducing mitral valve regurgitation.

The present invention, in some embodiments thereof, relates to methods and devices for reducing heart valve regurgitation for mitral valves as well as for tricuspid valves. For example, where example embodiments are provided with reference to two mitral valve leaflets, it is to be understood that the example embodiment may apply to the tricuspid clave with reference to three valve leaflets of the tricuspid valve.

Figure 1:
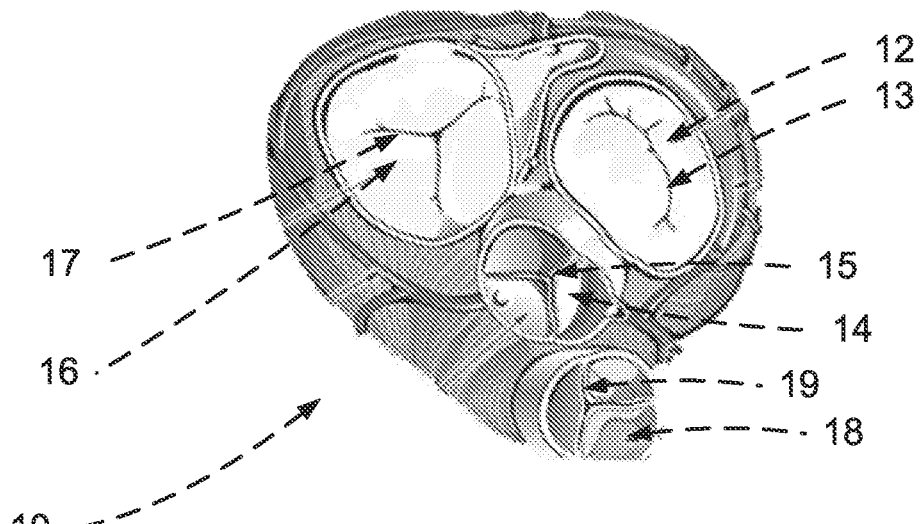
FIG. 1 is a simplified drawing of a top view of a cross section in a heart.

Reference is now made to FIG. 1, which is a simplified drawing of a top view of a cross section in a heart 10. The cross section depicts a mitral valve 12 and its coaptation line(s) 13, a tricuspid valve 16 and its coaptation lines 17, an aortic valve 14 and its coaptation lines 15 and a pulmonary (pulmonic) valve 18 and its coaptation lines 19.

In a natural heart, during closure of a cardiac valve, for example a mitral valve, anterior and posterior leaflets of the mitral valve close against each other in a region called the cooptation line. Along the coaptation line the leaflets interface tightly with each other to seal the mitral valve. In a diseased mitral valve the seal between the leaflets is damaged, and openings along the coaptation line allow leakage of blood through a mitral valve which is supposed to be closed.

In some embodiments a plug structure is placed between the leaflets. With the plug in place, the native leaflets close against the plug. During closure, the native anterior and posterior leaflets interface with the plug element, effectively creating new non-leaking cooptation lines.

An aspect of some embodiments enables treating mitral valve regurgitation with a device which potentially reduces regurgitation. Delivery and positioning of the device are relatively more rapid than current valve repair procedures, and the device potentially enables great reduction of cardiac valve regurgitation severity.

An aspect of some embodiments includes placing a plug structure between heart valve leaflets.

An aspect of some embodiments includes placing a structure between heart valve leaflets, which on the outer surface coapts with natural heart valve leaflets, and includes an inner surface defining a lumen containing a one-way valve. The one way valve is optionally open when blood flows in the downstream direction, and closes against blood regurgitating back upstream. The one way valve thus joins in the functioning of the natural heart valve.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 2A:
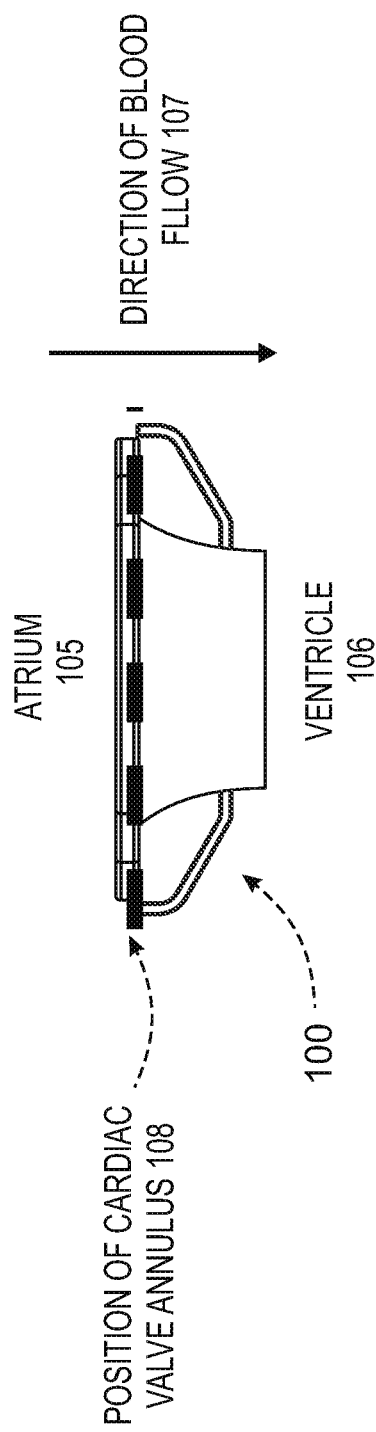
FIG. 2A is a side view of a device constructed according to an example embodiment of the invention.

Reference is now made to FIG. 2A, which is a side view of a device 100 constructed according to an example embodiment of the invention.

Figure 2C:
FIG. 2C is a photograph of the device of FIG. 2A in place in a mitral valve of a heart.
Figure 2B:
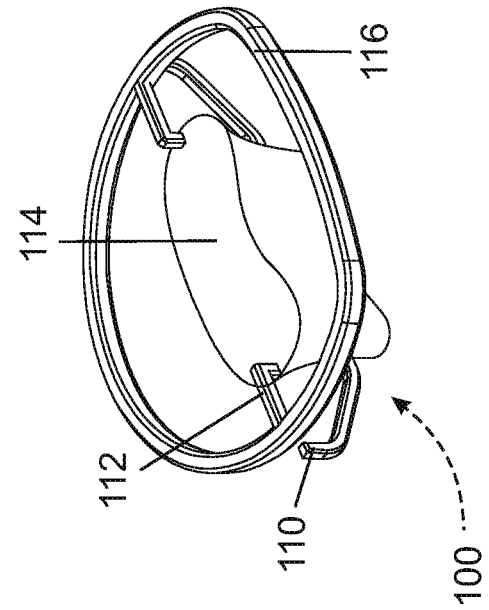
FIG. 2B is an isometric view of the device of FIG. 2A.

Reference is also made to FIG. 2B, which is an isometric view of the device 100 of FIG. 2A, and to FIG. 2C, which is a photograph of the device 100 of FIG. 2A in place in a mitral valve of a heart.

In some embodiments the device 100 includes a frame including a generally D-shaped ring 116 and two or more bridging elements 112 which are used to support a plug 114 element supported within the ring 116.

In some embodiment, two anchors 110 emerge from the plug 114 and are optionally used for attaching the device 100 to heart anatomy.

FIG. 2B shows an isometric view of the device 100, the D shaped ring 116, the plug 114 element, supported by the two bridging elements 112, and two anchors 110 attached to the plug 14.

FIG. 2A includes a line 108 depicting an optional position of a natural cardiac (mitral) valve annulus relative to device 100, when the device 100 is placed within a heart. The ring 116 of the device 100 optionally rests on top of the natural cardiac valve annulus, while the anchors 110 are optionally located below the annulus of the natural cardiac valve. FIG. 2A also depicts an arrow depicting a direction of blood flow 107: during diastole, blood flows from the left atrium 105, around the plug 114 structure, and into the left ventricle 106. During systole the cardiac valve leaflets (not shown) close against the plug 114, producing two non-leaking cooptation lines (pointed at by two arrows 120 121 in FIG. 2C). A first arrow 121 points at a first coaptation line (dotted line) on a mitral valve posterior leaflet side, and a second arrow 120 points at a second coaptation line (dotted line) on a mitral valve anterior leaflet side.

In some embodiments, a top of the plug 114 presents a stream-lined shape to the direction of blood flow 107.

In some embodiments, a top of the plug 114 may be higher than the line 108.

In some embodiments, a top of the plug 114 may be lower than the line 108.

In some embodiments a surgeon uses imaging of the heart in order to determine a relative height of the top of the plug 114 to the line 108. In some embodiments, the surgeon selects a device with a plug having such a height for insertion into the heart valve. In some embodiments the surgeon sets the height of the top of the plug relative to the height of the frame based, at least in part, on the imaging.

In some embodiments the plug 114 of the device 100 is shifted left or right, up or down, in a plane parallel to a plane of the ring 116, such that a center of the plug 114 is shifted relative to a center of the ring 116. The center is optionally defined as a center of mass, or a center of symmetry.

In some embodiments the plug 114 is optionally made of a flexible material, suitable for compression and insertion into the heart via a catheter.

In some embodiments, a length of the plug along a direction of blood flow 107 is at least 5 millimeters.

In some embodiments, a length of the plug along a direction of blood flow 107 is between 3 and 15 millimeters.

In some embodiments, the anchors 110 are located so as to be at heart valve commissures when the device 100 is in place in the heart.

In some embodiments, the anchors 110 are attached to the plug 114, as depicted in claim FIGS. 2A and 2B.

In some embodiments, the anchors 110 are attached to the ring 116 (not shown in FIGS. 2A and 2B).

In some embodiments, the anchors 110 are attached to the bridging elements 112 (not shown in FIGS. 2A and 2B).

In some embodiments, the device 100 includes two bridging elements 112 (as shown in FIGS. 2A and 2B).

In some embodiments, the device 100 includes one bridging element 112 (not shown in FIGS. 2A and 2B).

FIG. 2C shows that the device 100 allows a native mitral valve to close freely.

In some embodiments the device 100 is optionally designed to conform to natural mitral valve anatomy such that the natural mitral valve can continue its normal function.

In some embodiments the anchors 110 fix the device 100 in the region of the commissure of the natural cardiac valve, and below the annulus, such that the native leaflets are not affected.

In some embodiments the anchors 110 width is limited to 10 mm such that the anchors 110 may be inserted between chords found below natural mitral valve commissures. Wider anchors 110 might push against the chords, potentially damaging the natural mitral valve.

In some embodiments, a distance between distal ends of the anchors 110 is not larger than 60 mm.

Figure 3A:
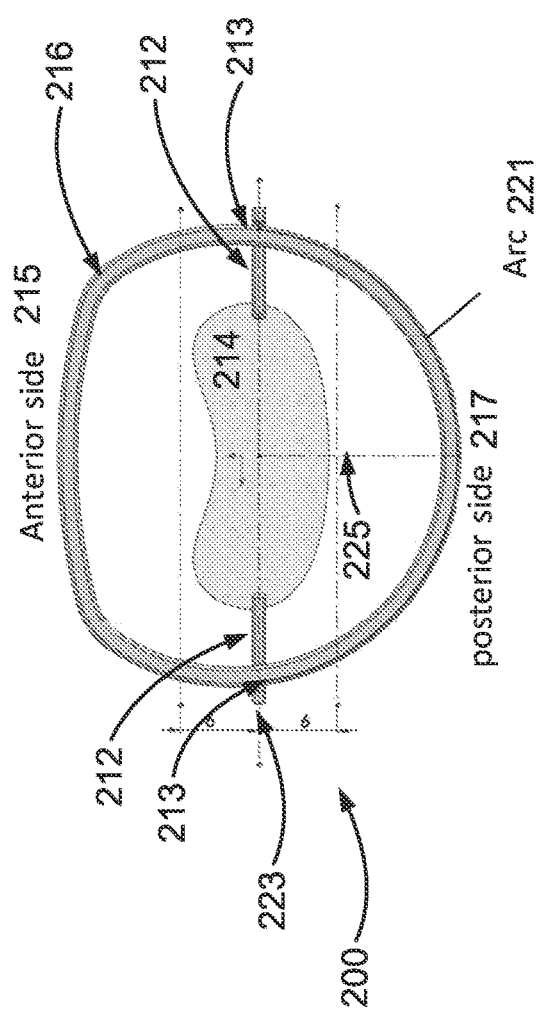
FIG. 3A is a top view of a device constructed according to an example embodiment of the invention.

Reference is now made to FIG. 3A, which is a top view of a device 200 constructed according to an example embodiment of the invention.

FIG. 3A shows a D-shaped ring 216, a plug 214 element, and bridging elements 212 connecting the plug 214 element and the D-shaped ring 216.

In some embodiments the device 200 also includes attachment wings (not shown) such as the anchors 110. By way of a non-limiting example, the attachment wings are optionally below the bridging elements 212 and not seen in a top-view of the device 200.

In some embodiments the attachment wings are located so as to pass through the commissures of a natural heart valve.

For example, FIG. 3A depicts an embodiment suitable for use in a mitral valve. The D-shape ring 216 has a distance between optional locations 213 of attachment wings of between 30-50 mm, and a distance between an anterior side 215 and a posterior side 217 of the ring 216 of 22-38 mm.

In some embodiments, a top of the plug 214 presents a stream-lined shape to the direction of blood flow.

In some embodiments the plug 214 of the device 200 is shifted left or right, up or down, in a plane parallel to a plane of the ring 216, such that a center of the plug 214 is shifted relative to a center of the ring 216.

In some embodiments, the plug 214 element width is optionally 20 mm and under, and its height is optionally between 5 and 25 mm.

In some embodiments, the plug 214 element has a rounded, optionally kidney-like shape. A side of the plug 214 facing the anterior leaflet optionally has a concave shape, while a side of the plug 214 facing the posterior leaflet has a convex shape. This design potentially enables aligning the plug shape with a cooptation line of the native mitral valve leaflets.

FIG. 3A shows a position of attachment wing locations 213 relative to the ring 216. In the example embodiment depicted in FIG. 3A, a horizontal line 223 crosses locations of the attachment wings, and a vertical line 225 passes through the center of the horizontal line 223 and through a center of a posterior-side arc 221 of the ring 216.

In some embodiments, in order to position attachment wings below small leaflets of native mitral valve, the attachment wings are not be more than 6 mm distant from the vertical line 225.

In some embodiments, the bridging elements 212 are at the center line 223 of the plug 214 element.

Figure 3C:
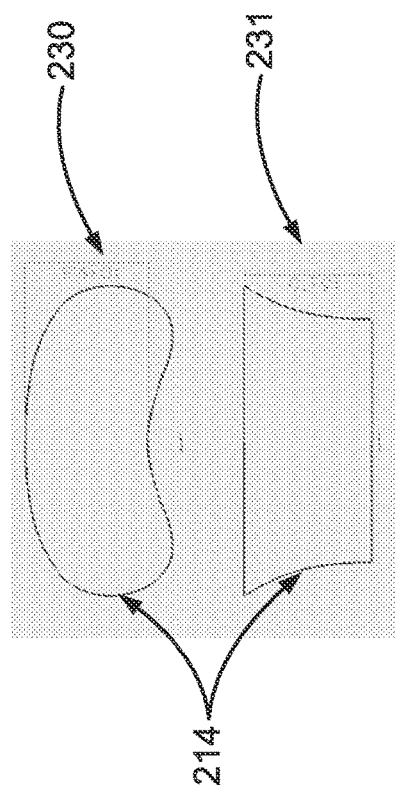
FIG. 3C is a top view of the plug element of FIG. 3A and a side view of the plug element of FIG. 3A.
Figure 3B:
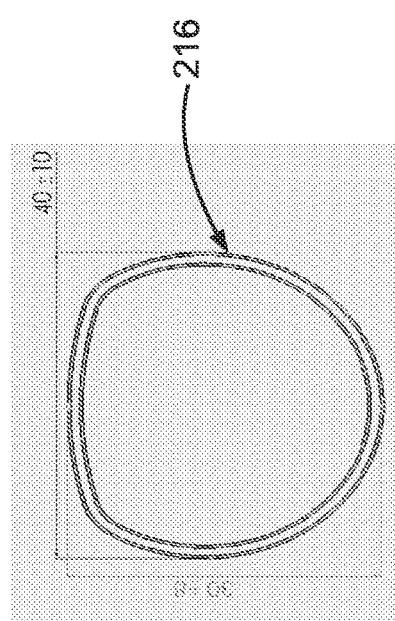
FIG. 3B is a top view of the ring of FIG. 3A.

Reference is now made to FIG. 3B, which is a top view of the ring 216 of FIG. 3A.

Reference is now made to FIG. 3C, which is a top view 230 of the plug 214 element of FIG. 3A and a side view 231 of the plug 214 element of FIG. 3A.

Reference is now made to FIG. 4A, which is a simplified isometric line drawing of a wire frame construction 300 which forms part of a device constructed according to an example embodiment of the invention.

FIG. 4A depicts a ring 302, and a plug element made of a top frame 320 and a bottom frame 322, optionally attached to each other by commissure extensions 324.

The wire frame construction 300 depicted in FIG. 4A includes a wire-frame construction, which may optionally be made of a flexible material, suitable for insertion into the heart via a catheter.

In some embodiments, the wire frame construction 300 is optionally made of Nitinol.

In some embodiments the plug element may optionally be made of a flexible material, suitable for compression and insertion into the heart via a catheter.

Reference is now made to FIG. 4B, which is a simplified isometric line drawing of the wire frame construction 300 of FIG. 4A and an additional plug cover 326 material.

In some embodiments, a plug element cover 326 is optionally manufactured and/or sutured onto the top frame 320 and the bottom frame 322.

In some embodiments, the cover 326 is optionally made of pericard, polyester, nylon.

Reference is now made to FIG. 4C, which is an isometric view of a device 330 constructed according to another example embodiment of the invention.

The device depicted in FIG. 4C includes a frame 333 similar to the frame of FIG. 4A, and a different plug element 338 shape.

Until now, the plug elements have been described with reference to reducing or eliminating mitral regurgitation, which is a backward flow of blood through the mitral valve. However, the plug elements may optionally also be designed to reduce resistance to forward flow.

The design depicted in FIG. 4C depicts a plug element 338 shape which, in the portion facing blood flow has a hemodynamic structure designed to facilitate blood flow. The hemodynamic shape provides for a smoother more laminar flow of blood, poses less resistance to flow, and potentially minimizes a reduction in blood inflow during diastole caused by the adding a plug element to a natural cardiac valve.

Reference is now made to FIG. 5, which is an isometric view of a device 400 constructed according to yet another example embodiment of the invention.

FIG. 5 depicts a plug element which includes a one way artificial valve 430 made of flexible material which acts as a one way valve. The valve 430 optionally includes a flexible tube which can collapse to close against backward blood flow, or two or more leaflets which shut against backward blood flow.

In some embodiments the artificial valve 430 is optionally made from pericard, and optionally sutured to a frame such as the top frame 320 of FIG. 4A, and/or to frame extensions 324 such as the commissure extensions 324 of FIG. 4A.

A potential advantage of using an artificial one way valve configuration is that potentially reduces or eliminates resistance to inflow of blood during diastole.

The artificial valve may be produced from synthetic materials or from natural materials. The term artificial valve is used herein to mean a valve in addition to a natural cardiac valve which includes the natural leaflets naturally attached to the heart.

Figure 6A:
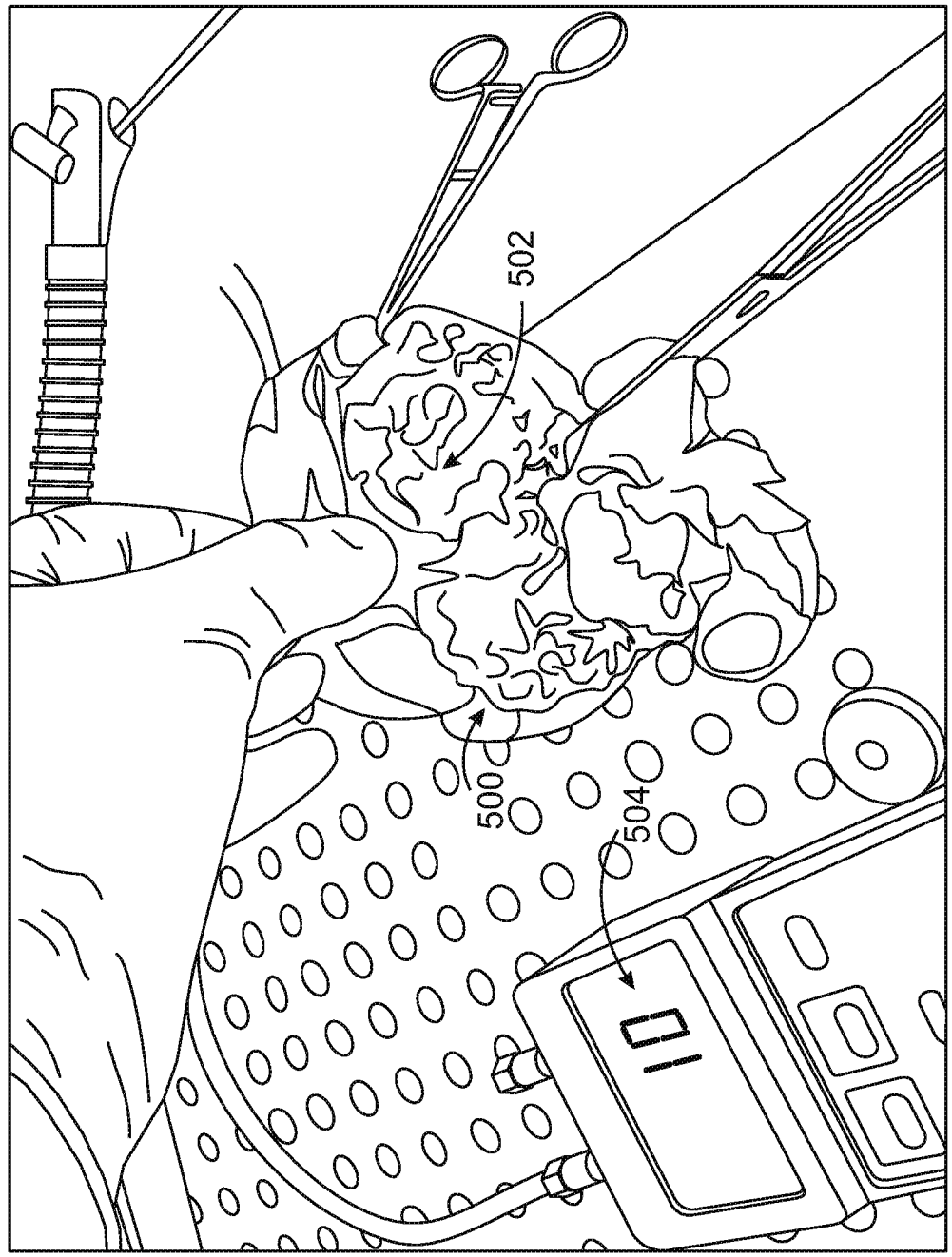
FIGS. 6A and 6B are photographs of a proof-of-concept bench test for an example embodiment of the invention.
Figure 6B:
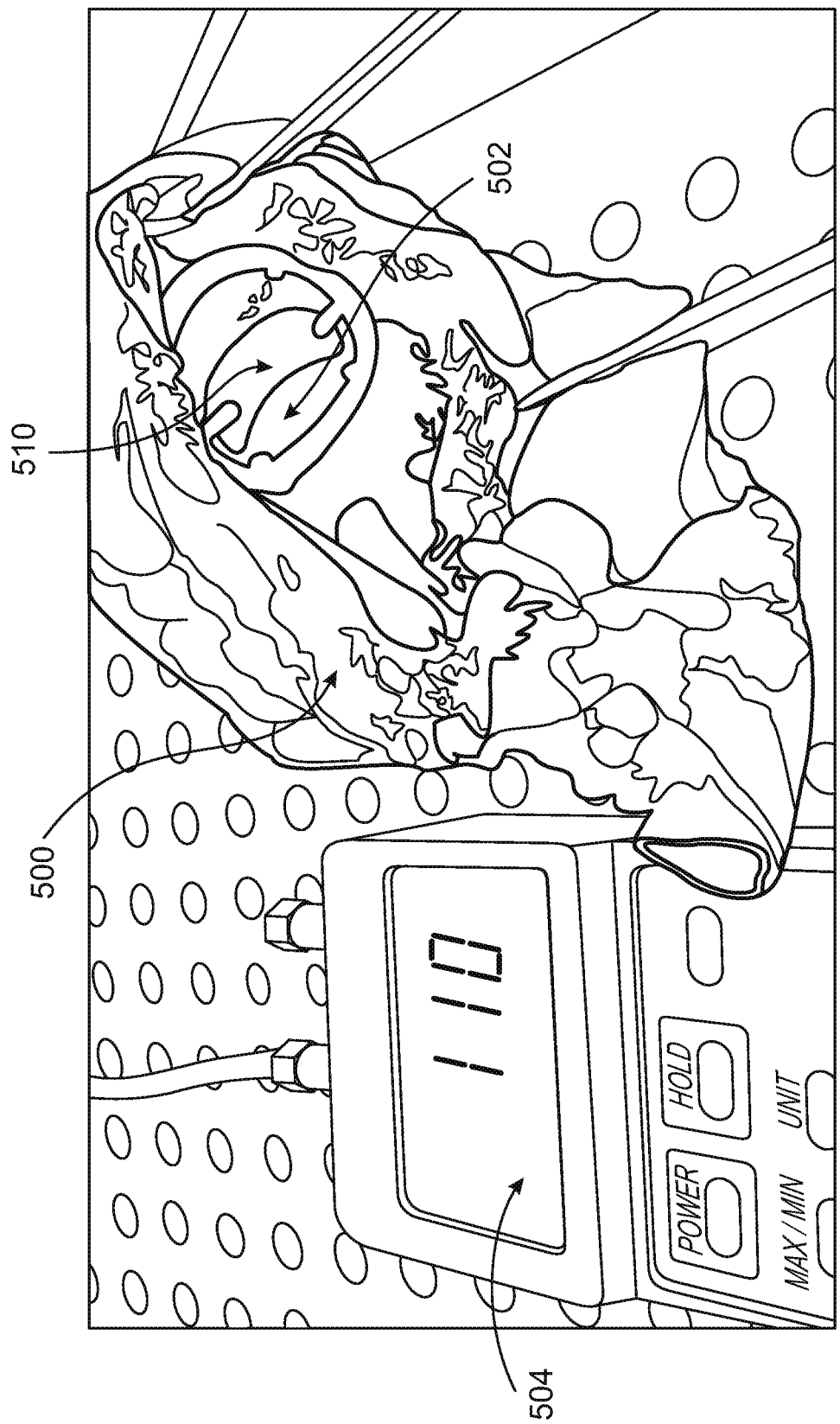

Reference is now made to FIGS. 6A and 6B, which are photographs of a proof-of-concept bench test for an example embodiment of the invention.

In the proof-of-concept bench test a mitral regurgitation model was created in a pig heart by tearing a few cords connected to the native leaflets of the mitral valve. The aorta outflow was blocked and the heart left ventricle was connected to a water source. Pressure measurement across the mitral valve was recorded.

FIG. 6A depicts a pig heart 500 with a damaged mitral valve 502 connected to a water flow source (not shown), and a pressure meter 504 showing very little pressure build up across the mitral valve due to mitral leakage. The pressure meter 504 depicts about 10 mmHg pressure.

FIG. 6B depicts the pig heart 500 with the damaged mitral valve 502 connected to a water flow source (not shown), and the pressure meter 504.

FIG. 6B also shows a device 510 similar to the device depicted in FIGS. 2A, 2B, 2C placed in the damaged mitral valve 502.

FIG. 6B shows that positioning the device 510 in the mitral valve repaired mitral regurgitation. Leakage was completely stopped, and pressure across mitral was recorded to be about 110 mmHg.

Figure 7:
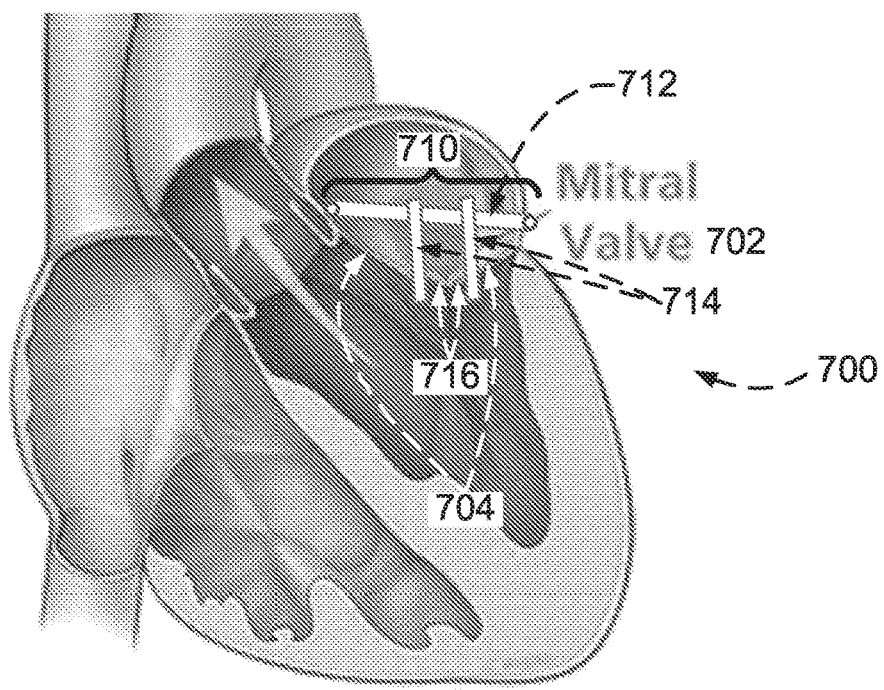
FIG. 7 is a simplified cross section view of a heart with a device for reducing mitral valve regurgitation according to an example embodiment of the invention.

Reference is now made to FIG. 7, which is a simplified cross section view of a heart 700 with a device 710 for reducing mitral valve regurgitation according to an example embodiment of the invention.

FIG. 7 is intended to present a general structure of the device 710 in place relative to an example heart valve—the mitral valve 702.

FIG. 7 depicts the example embodiment device 710 as generally including a frame 712 and frame extensions 714. The frame 712 and/or the frame extensions 714 are optionally attached to a one way valve, and FIG. 7 depicts leaflets 716 of the one way valve.

FIG. 7 depicts native leaflets 704 sealing against the frame extensions 714 and/or the one way valve of the device 710, and/or the device 710 body.

The one way valve is optionally placed inside the body of the device 710.

Figure 8:
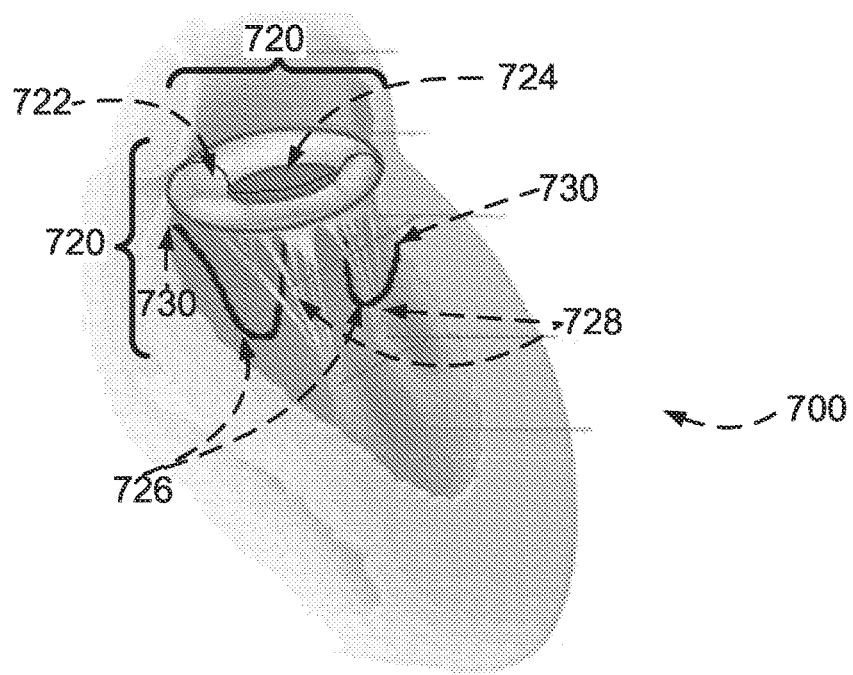
FIG. 8 is a simplified cross section view of a heart with a device for reducing mitral valve regurgitation according to another example embodiment of the invention.

Reference is now made to FIG. 8, which is a simplified cross section view of a heart 700 with a device 720 for reducing mitral valve regurgitation according to another example embodiment of the invention.

FIG. 8 depicts the device 720 located approximately in a centre of the native mitral valve so as to allow native leaflets (not shown) to seal against the device 720.

The device includes a frame 722, and a one way valve 724.

In some embodiments, the device 720 includes anchoring extensions 726, which optionally extend under cusps, cross between chordae 728, and optionally reach the heart wall 730. The anchoring extensions 726 potentially allow the chordae 728 and leaflets (not shown) to retain their natural motion and potentially most or all of their range of motion.

In some embodiments a surface area the device 720 present to backward blood pressure during systole is smaller than the surface area presented by the entire mitral valve, resulting in potentially less force acting on the device 720 than on an entire mitral valve under the same pressure conditions.

Reference is now made to FIGS. 9A-9G, which are simplified illustrations of a device 900 for reducing mitral valve regurgitation according to still another example embodiment of the invention.

FIGS. 9A-9D depicts isometric views of the device 900 from several viewpoints.

FIGS. 9E-9G depict cross sectional views of the device 900.

FIGS. 9A-9G depicts the following components of the device 900:

a ring 916;

a plug 914 element;

bridging elements 912 connecting the plug 914 element and the ring 916;

anchor extensions 910.

In some embodiments the plug 914 is optionally a flexible tube, which shuts under pressure and acts as a one way valve preventing retrograde blood flow during systole.

In some embodiments, the device 900 includes three anchor extensions 910.

In some embodiments, the device includes an anterior support arch (not shown) configured to pass behind an anterior mitral valve leaflet, optionally providing support by pressing against or attaching to mitral valve trigons and/or pressing against the heart wall.

In some embodiments, the device includes a posterior support arch (not shown) configured to pass behind a posterior mitral valve leaflet, optionally providing support by pressing against the heart wall.

In some embodiments an additional one way valve is optionally placed inside the plug 914 of the device 900.

In some embodiments the ring 916 optionally includes screws and/or hooks for attaching to the cardiac valve annulus.

In some embodiments the ring 916 is optionally sutured to the cardiac valve annulus.

Figure 10:
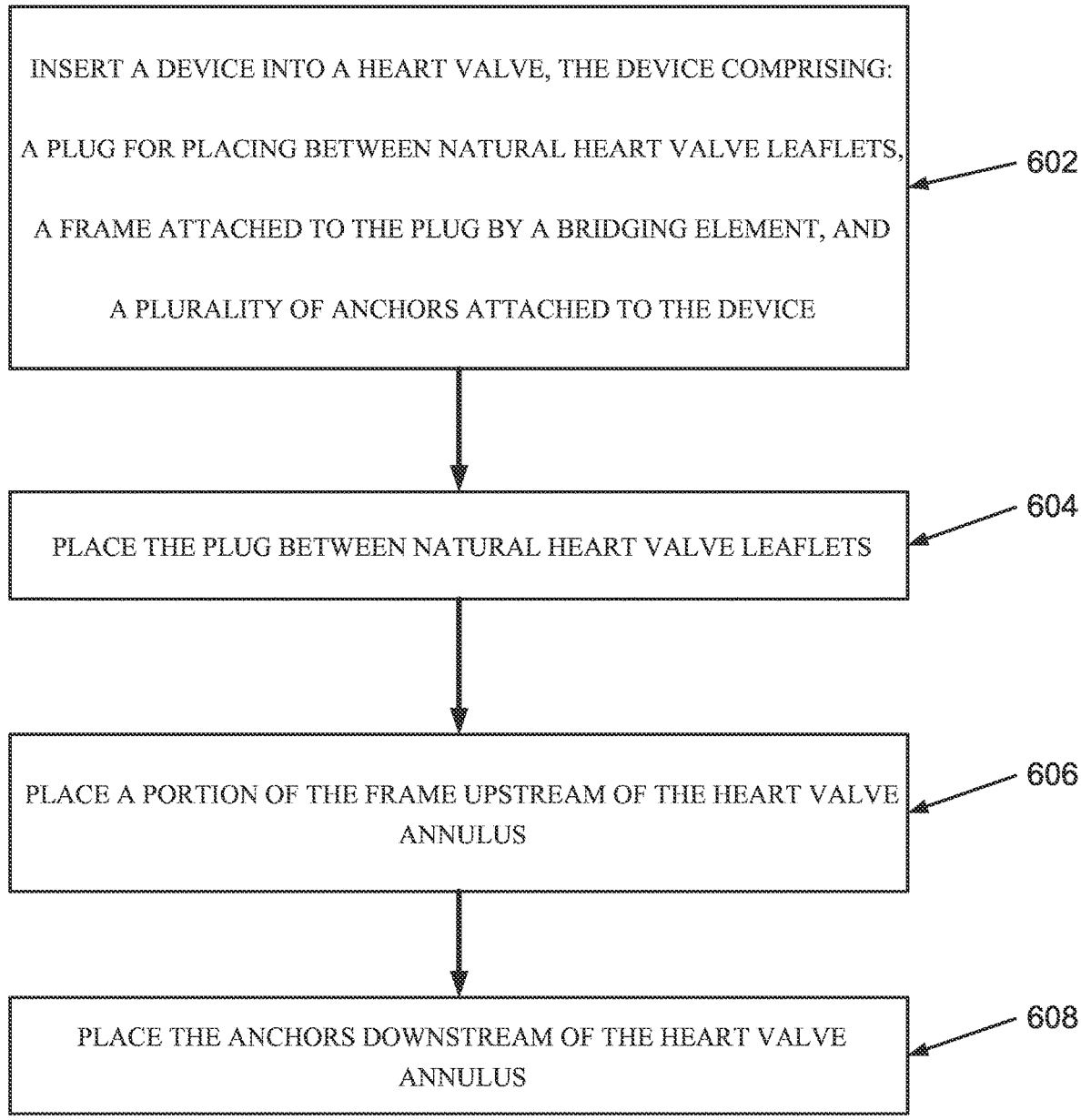
FIG. 10 is a simplified flow chart illustration of a method for reducing heart valve regurgitation according to an example embodiment of the invention.

Reference is now made to FIG. 10, which is a simplified flow chart illustration of a method for reducing heart valve regurgitation according to an example embodiment of the invention.

FIG. 10 depicts a method comprising:

inserting a device into a heart valve (602), the device comprising: a plug for placing between natural heart valve leaflets, the plug shaped so that, upon systole, the natural heart leaflets coapt upon the plug; a frame attached to the plug by a bridging element, for supporting the plug between the natural heart valve leaflets, the frame having at least one dimension in a plane of the heart valve annulus which is wider than the diameter of the heart valve annulus; and a plurality of anchors attached to the device, for preventing the device plug from being swept upstream of the heart valve annulus upon systole;

placing the plug between natural heart valve leaflets (604);

placing a portion of the frame upstream of the heart valve annulus (606); and placing the anchors downstream of the heart valve annulus (608).

It is expected that during the life of a patent maturing from this application many relevant artificial cardiac valves will be developed and the scope of the term artificial cardiac valves is intended to include all such new technologies a priori.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for reducing heart valve regurgitation comprising:

a plug for placing between natural heart valve leaflets, the plug shaped so that, upon systole, the natural heart leaflets coapt upon the plug;

a frame shaped as a planar D-shaped ring attached to the plug by a bridging element, for supporting the plug between the natural heart valve leaflets, the frame having at least one dimension above the heart valve annulus which is wider than the diameter of the heart valve annulus; and a plurality of anchors attached to the device, for preventing the device from being swept upstream of the heart valve annulus upon systole, wherein:

the plug has an elongate cross-sectional shape parallel to a plane of the D-shaped ring;

the anchors emerge radially from sides of the plug, at elongate ends of the elongate cross-sectional shape of the plug, along an elongation direction of the elongate cross-sectional shape of the plug, and turn toward the frame; and the anchors are attached to the plug at locations so as to be at heart valve commissures when the device is in placed in the heart.

2. The device of claim 1, in which a cross section of the plug perpendicular to a direction of blood flow is kidney-shaped.

3. The device of claim 1, in which a top of the plug is higher than the frame relative to a direction of blood flow.

4. The device of claim 1, in which a top of the plug is lower than the frame relative to a direction of blood flow.

5. The device of claim 1, in which the bridging element comprises two bridging elements.

6. The device of claim 1, in which;
a top of the frame is at a level of a top of the plug relative to a direction of blood flow; and
a bottom of the frame is higher than a bottom of the plug relative to the direction of blood flow.

7. The device of claim 1, in which the anchors are arranged to engage a bottom of the heart valve annulus.

8. The device of claim 1 wherein the bridging element bridges the gap between the frame and the plug.

9. The device of claim 1 wherein the plug comprises a one-directional flow valve.

10. A method for reducing heart valve regurgitation comprising:
inserting a device into a heart valve, the device comprising:
a plug for placing between natural heart valve leaflets, the plug shaped so that, upon systole, the natural heart leaflets coapt upon the plug;
a frame shaped as a planar D-shaped ring attached to the plug by a bridging element, for supporting the plug between the natural heart valve leaflets, the frame having at least one dimension above the heart valve annulus which is wider than the diameter of the heart valve annulus; and
a plurality of anchors attached to the device, for preventing the device plug from being swept upstream of the heart valve annulus upon systole,
wherein:
the plug has an elongate cross-sectional shape parallel to a plane of the D-shaped ring;
the anchors emerge radially from sides of the plug, at elongate ends of the elongate cross-sectional shape of the plug, along an elongation direction of the elongate cross-sectional shape of the plug, and turn toward the frame and
the anchors are attached to the plug at locations so as to be at heart valve commissures when the device is in place in the heart;
placing the plug between natural heart valve leaflets;
placing a portion of the frame upstream of the heart valve annulus; and
placing the anchors downstream of the heart valve annulus.

11. The method of claim 10 in which the placing the anchors downstream of the heart valve annulus comprises placing the anchors downstream of the heart valve annulus at locations of the heart valve commissure.

12. The method of claim 10 in which a surgeon uses imaging of the natural heart in order to determine a height, relative to a direction of blood flow, of a top of the plug relative to a height of the frame, and selects a device with a plug having such a height for insertion into the heart valve.

13. The method of claim 10 in which a surgeon uses imaging of the natural heart in order to determine a height, relative to a direction of blood flow, of a top of the plug relative to a height of the frame, and sets the height of the top of the plug relative to the height of the frame based, at least in part, on the imaging.

14. The method of claim 10 in which the heart valve is the mitral valve and the plug is kidney-shaped.

15. The method of claim 10 in which the heart valve is the mitral valve and the device comprises two anchors.

16. The method of claim 15 in which the two anchors are located so as to pass through the mitral valve at commissures of the mitral valve.

17. The method of claim 10, in which the placing the anchors downstream of the heart valve annulus comprises placing the anchors to engage a bottom of the heart valve annulus.

18. A device for reducing heart valve regurgitation comprising:
a plug for placing between natural heart valve leaflets, the plug shaped so that, upon systole, the natural heart leaflets coapt upon the plug and the plug having an elongate cross-sectional shape perpendicular to a direction of blood flow;
a frame shaped as a planar D-shaped ring attached to the plug by a bridging element, for supporting the plug between the natural heart valve leaflets, the frame having at least one dimension above the heart valve annulus which is wider than the diameter of the heart valve annulus;
anchors emerging radially from sides of the plug, at elongate ends of the elongate cross-sectional shape of the plug, along an elongation direction of the elongate cross-sectional shape of the plug, and turn toward the D-shaped ring and the anchors are attached to the plug at locations so as to be at heart valve commissures when the device is in place in the heart.

19. The device of claim 18 wherein the bridging element bridges the gap between the frame and the plug.

* * * * *